United States Patent [19]

Henry et al.

[11] 4,109,076

[45] Aug. 22, 1978

[54] 5-IMINODAUNOMYCIN

[75] Inventors: David W. Henry, Chapel Hill, N.C.; George L. Tong, Cupertino, Calif.

[73] Assignee: SRI International, Menlo Park, Calif.

[21] Appl. No.: 831,438

[22] Filed: Sep. 8, 1977

[51] Int. Cl.[2] .................. C07G 3/00; C07G 11/00
[52] U.S. Cl. ......................... 536/4; 536/17; 424/180
[58] Field of Search ...................... 536/4, 17

[56] References Cited

U.S. PATENT DOCUMENTS 3,803,124  4/1974  Arcamone et al. ............ 536/17

Primary Examiner—Ethel G. Love
Attorney, Agent, or Firm—Donovan J. De Witt

[57] ABSTRACT

5-Iminodaunomycin having good antitumor activity coupled with low cardiotoxicity.

2 Claims, No Drawings

5-IMINODAUNOMYCIN

The invention described herein was made in the course of or under a contract with the U.S. Department of Health, Education, and Welfare.

SUMMARY OF THE INVENTION

The present invention relates to the novel compound 5-iminodaunomycin having the structure,

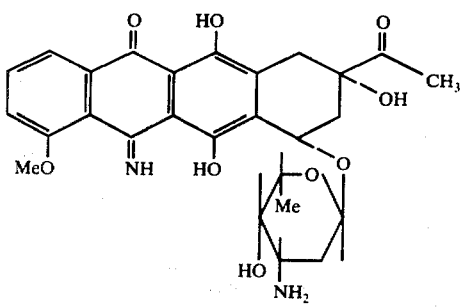

together with its pharmaceutically acceptable salts, as formed with the —$NH_2$ group of the sugar moiety.

The preparation of the hydrochloride salt of the above identified compound is set forth below in the example. Biological test data showing the good antitumor characteristics of the aforesaid compound and its low cardiotoxicity, as compared with that of adriamycin and daunomycin, are presented below.

EXAMPLE

5-Iminodaunomycin Hydrochloride

To a stirred solution of 1700 ml of methanolic ammonia (saturated at 0°) cooled in an ice bath was added a solution of 28.76 g (51 mmol) of daunomycin hydrochloride in 500 ml of methanol. The solution was stirred in the ice bath for 1 hour and then stored at 0°–5° for 39 hours. The reaction mixture was evaporated; the residue was dissolved in 400 ml of chloroform-methanol (4:1) and re-evaporated thrice to afford 33.88 g of a violet residue. The residue was purified by column chromatography (2600 g of 200-325 mesh silica gel; $CHCl_3$—$CH_3OH$ 6:1) to afford 18.32 g of product. The product was dissolved in 190 ml of chloroform-methanol, the solution was stirred and 760 ml of ether was added dropwise. The resulting precipitate was collected, washed with ether and dried to give 16.78 g (57%) of 5-iminodaunomycin hydrochloride as a bluish-violet powder, mp 175°–178° dec., IR (Nujol) 2.92 μm (OH), 5.82 (C=O), 6.31 (C=O, chelated quinone). UV-Vis max ($CH_3OH$) 220 nm (ε 29,800), 233 sh (24,600), 252 (32,000), 307 (6,930), 335 sh (4,290), 357 sh (3,940), 472 sh (2,560), 520 sh (8,790), 551 (16,600), 592 (19,800), NMR 100 MHz ($DMSOd_6$) 13.43 δ (bs, 1, OH-11), 9.47 (bs, 1, OH-6), 7.2–9.0 (3, N⊕$H_3$), 7.91 (d, 1, J=8Hz, H-1), 7.75 (t, 1, J=8Hz, H-2), 7.53 (d, 1, J=8Hz, H-3), 5.47 (bs, 1, H-1'), 5.42 (s, 2, OH-4',9), 4.94 (m, 1, H-7), 4.20 (m, 1, H-5'), 4.10 (s, 3, $OCH_3$), 3.65 (m, 1, H-4'), 2.83 (bs, 2, H-10), 2.31 (s, 3, H-14), 2.08 (m, 2, H-8), 1.79 (m, 2, H-2'), 1.18 (d, 3, J=6Hz, $CH_3$-5').

|  | C | H | $Cl^\theta$ | N |
|---|---|---|---|---|
| Anal. Calc for $C_{27}H_{30}N_2O_9 \cdot HCl \cdot H_2O$ | 55.82 | 5.72 | 6.10 | 4.82 |
| Found | 56.13 | 5.65 | 5.96 | 4.83 |

The compound of the present invention is preferably employed in salt form since it then has adequate solubility in water. However, said compound can be employed in the non-salt form if so desired.

These addition salts (shown herewith as that of HCl) are preferably the pharmaceutically acceptable, non-toxic addition salts with suitable acids, such as those with inorganic acids, for example, hydrochloric, hydrobromic, nitric, sulphuric and phosphoric acids, and with organic acids, such as organic carboxylic acids, for example, glycolic, maleic, hydroxymaleic, malic, tartaric, citric, salicylic acids, and organic sulphonic acids, for example, methanesulphonic and toluene-p-sulphonic acids.

An acid addition salt can be converted into the free compound according to known methods, for example, by treating it with a base, such as an alkali metal or alkaline earth metal hydroxide, for example, lithium hydroxide, sodium hydroxide, potassium hydroxide or calcium hydroxide; with a metal carbonate, such as an alkali metal or an alkaline earth metal carbonate or hydrogen carbonate, for example sodium, potassium or calcium carbonate or hydrogen carbonate; with ammonia; or with a hydroxyl ion exchange resin, or with any other suitable reagent.

An acid addition salt may also be converted into another acid addition salt according to known methods; for example, a salt with an inorganic acid may be treated with a metal salt, for example, a sodium, barium or silver salt, of an acid in a suitable diluent, in which a resulting inorganic salt is insoluble and is thus removed from the reaction medium. An acid addition salt may also be converted into another acid addition salt by treatment with an anion exchange preparation.

The compound of this invention (and its salts) can be formulated as novel pharmaceutical preparations together with conventional pharmaceutical organic or inorganic carrier materials suitable for internal administration. Such preparations can be administered parenterally or orally, the dosages to be adjusted according to individual requirements. The novel pharmaceutical compositions can contain such conventional organic or inorganic inert carrier materials as water, gelatin, lactose, starch, magnesium stearate, talc, vegetable oils, gums, polyalkylene glycols, vaseline or the like. The pharmaceutical preparations can be in the conventional solid forms such as tablets, dragees, suppositories, capsules or in conventional liquid form such as solutions, suspensions of emulsions. The pharmaceutical compositions can be submitted to conventional pharmaceutical expedients such as sterilization and/or can contain conventional pharmaceutical additives such as preservatives, stabilizing agents, wetting agents, emulsifying agents, salts for adjusting the osmotic pressure, buffers or the like. They also can contain other therapeutically useful materials.

BIOLOGICAL TESTS

Biological testing data for the compound of this invention, as the HCl salt, and for adriamycin and daunomycin are present in the table given below. Such data were obtained when these compounds were tested against lymphocytic leukemia P388 implanted in mice under the auspices of the NCI and according to protocols which use the increased survival time of treated animals compared to controls as the measure of antitumor efficacy. Also included in the table are results obtained in the cardiotoxic evaluation of the indicated compounds in a reproducible screening system employing the rat, the data so obtained being referred to as the minimum cumulative cardiotoxic dose (MCCD). In these tests the rat model employs as end point the characteristic electrocardiographic changes that follow repeated administration of cardiotoxic anthracycline derivatives.

| Compound | NSC[a] No. | Cardiotoxicity in Rats[b] Minimum Cumulative Cardiotoxic Dose mg/kg | Activity vs Leukemia P388 in Mice[c] $q^4d$ 5,9,13 | |
|---|---|---|---|---|
| | | | Increased Survival Time % T/C | Optimum Dose mg/kg |
| Daunomycin | 82151 | 14 | 135 | 4.0 |
| Adriamycin | 123127 | 11 | 150 | 4.0 |
| 5-imino- | | | 136 | 3.0 |
| daunomycin | 254681 | 64 | 133 | 1.5 |

[a]Accession number of the National Cancer Institute.
[b]Assay described in G. Zbinden and E. Brandle, Cancer Chemo. Rpts., Part 1, 59, 707 (1975)
[c]Ip P388 murine leukemia treated ip on Q4D 5, 9, 13 schedule according to standard NCI protocols. Assay described in R. I. Geran, N. H. Greenberg, M. M. MacDonald, A. M. Schumacker and B. J. Abbott, Cancer Chemother. Rep., of treated mice to that of untreated controls times 100. Untreated controls survive about 9 days.

We claim:
1. 5-Iminodaunomycin and its pharmaceutically acceptable acid addition salts.
2. The compound of claim 1 which is 5-iminodaunomycin hydrochloride.

* * * * *

UNITED STATES PATENT AND TRADEMARK OFFICE
CERTIFICATE OF CORRECTION

PATENT NO. : 4,109,076
DATED : August 22, 1978
INVENTOR(S) : DAVID W. HENRY and GEORGE L. TONG It is certified that error appears in the above-identified patent and that said Letters Patent are hereby corrected as shown below:

Add the following language at the end of line 5, column 1:

> The Government has rights in this invention pursuant to Contract No. N01-CM-33742.

Change footnote c of the table appearing on the last page of the patent as follows that the language may read as it does in the patent application:

c  Ip P388 murine leukemia treated ip on Q4D 5, 9, 13 schedule according to standard NCI protocols. Assay described in R. I. Geran, N. H. Greenberg, M. M. MacDonald, A. M. Schumacker and B. J. Abbott, <u>Cancer Chemother. Rep.</u>, Part 3, 3 (No.2), 9 (1972), Protocol 1,200. T/C = ratio of survival time of treated mice to that of untreated controls times 100. Untreated controls survive about 9 days.

Signed and Sealed this

Sixth Day of May 1980

[SEAL]

Attest:

SIDNEY A. DIAMOND

*Attesting Officer*   *Commissioner of Patents and Trademarks*